United States Patent [19]

Kawashima et al.

[11] Patent Number: 4,999,058
[45] Date of Patent: Mar. 12, 1991

[54] LACTITOL TRIHYDRATE CRYSTAL, CRYSTALLINE MIXTURE SOLID CONTAINING IT AND PROCESS FOR PREPARING THEM

[75] Inventors: Shigeru Kawashima; Hiroshi Ide, both of Shizuoka; Kazuaki Kato, Saitama; Mitsuo Magara; Yoshibumi Ishii, both of Shizuoka, all of Japan

[73] Assignee: Towa Chemical Industry Co., Ltd., Tokyo, Japan

[21] Appl. No.: 469,342

[22] Filed: Jan. 24, 1990

[30] Foreign Application Priority Data

Jan. 31, 1989 [JP] Japan ................................. 1-19451

[51] Int. Cl.$^5$ ............................................. C07H 15/08
[52] U.S. Cl. ...................................... 127/29; 426/658
[58] Field of Search ................ 127/29, 30; 426/658; 536/1.1

[56] References Cited

U.S. PATENT DOCUMENTS 3,957,976 5/1976 Sugimoto ............................ 514/53
3,973,050 8/1976 Hayashibara ...................... 426/552

FOREIGN PATENT DOCUMENTS 0039981 11/1981 European Pat. Off. ............. 127/29
2133428 1/1973 Fed. Rep. of Germany .

OTHER PUBLICATIONS

Journal of Agricultural and Food Chemistry, vol. 27, 1979; pp. 680–686, J. A. Van Velthuijsen "Food Additives—Lactitol Palmitate".

Primary Examiner—Theodore Morris
Assistant Examiner—David M. Brunsman
Attorney, Agent, or Firm—Beveridge, DeGrandi & Weilacher

[57] ABSTRACT

The present invention is to solve a variety of problems relative to conventional lactitol crystals and relates to a trihydrate crystal of lactitol having a molecular formula $C_{12}H_{24}O_{11}\cdot 3H_2O$ and a melting point of 52°–56° C., a crystalline mixture solid containing it and a process for producing them.

8 Claims, 1 Drawing Sheet

LACTITOL TRIHYDRATE CRYSTAL, CRYSTALLINE MIXTURE SOLID CONTAINING IT AND PROCESS FOR PREPARING THEM

BACKGROUND OF THE INVENTION

The present invention relates to a lactitol trihydrate crystal, a crystalline mixture solid containing it and a process for preparing them.

Lactitol is a product of lactose of which glucose moiety has been reduced into sorbitol and is designated as 4-β-D-galactopyranosyl-D-sorbitol.

Lactitol and conventional methods for producing it are described in J. Agricultural and Food Chemistry, 27, 4, 680–686 (1979), in which a 30–40% by weight aqueous lactose solution as a starting material is hydrogenated under the condition of hydrogen pressure of 40 atm at 100° C. in the presence of Raney nickel and the catalyst was then settled and removed by filtration to give a product after purification with ion exchange resin or activated carbon, etc.

Lactitol thus obtained has a relative sweetness of 36% on comparison based on the 100% of a 5% aqueous sucrose solution with a lactitol solution having the same concentration, and the sweetness of lactitol is lower than that of sorbitol (relative sweetness 65%) or xylitol (relative sweetness 96%).

West-German Patent (MEIZENA, 1974) discloses that lactitol is hydrolyzed with α-glucosidase (maltase) substantially slower than lactose or maltose.

For instance, lactose is hydrolyzed almost completely by β-galactosidase within 45 min, while lactitol is hydrolyzed only to a level of 10–15% within 45 min.

Thus, lactitol is hardly absorbable and utilizable in the digestive system or scarcely fermented by intrabuccal bacteria, so that it is soluble for a sweetening source of low-caloric foods, dietary foods, low cariogenic foods, health foods or the like which are ingested by diabetics, obese persons or those who are cautious of diseases in adults or dental caries.

Lactitol has a hygroscopicity lower than sorbitol, glycerol, xylitol or the like and, as aldehyde group being reduced, stability to heat or alkali, so that it can be advantageously used for a variety of foods.

Lactitol crystals are described in several literatures. For example, a crystal of lactitol dihydrate having a melting point of 76–78° C. and a specific rotation of +12.2° C. and an anhydrous crystal of lactitol having a melting point of 146° C. and a specific rotation of +14° C. are described in Comptes Rendus Hebdomadaries des Séances de l'Académie des Sciences, 170, 47–50 (1920) and J. Am. Chem. 74, 1105 (1952).

Moreover, a crystal of lactitol monohydrate is described in J. Agricultural and Food Chemistry, 27, 4, 680–686 (1979), in which a crystal of lactitol containing 1% of lactulitol (4-β-D-galactosyl-D-mannitol) and 3% of mannitol is disclosed.

However, conventional anhydrous crystals of lactitol, lactitol monohydrate, lactitol dihydrate and methods for producing them have a variety of disadvantages in the production or application, and it has been earnestly desired to eliminate these disadvantages.

That is to say, the anhydrous crystal of lactitol in the prior art has many problems (i) in production that a relatively difficult drying process or tedious procedures are required; (ii) in properties that the anhydrous lactitol is relatively hygroscopic and absorbs humidity in the atmosphere to deteriorate its quality with the passage of time when such a packaging material or a container as used in other anologous sugar alcohols such as an anhydrous crystal of maltitol or the like are used; or (iii) in application that the anhydrous lactitol has a high melting point, and it should be heated to a high temperature when it is used as a dispersant of other powdered materials, so that the other components tends to be decomposed.

On the other hand, the lactitol monohydrate crystal which has hitherto been known in the art has problems that it contains impurities such as mannitol, lactulitol or the like and has bitter taste, so that it is not suitable for food, that it has a high melting point in the range of 94–97° C. and thus feels rough at a temperature of ca. 60° C. or that when the preparation of the crystal is tried for the reproduction test of it, the quality control of it is hard.

Moreover, dihydrate crystals of lactitol has also problems that it has the melting point of 76–78° C., which is too high for the crystals to be dissolved when powdered on a warm food on a table, or that it has rough mouth feel and thus has an undesirable feeling on eating, so that the use of it for food are restricted.

Thus, there have been desired the improvements of the aforementioned problems for the crystals of lactitol.

We have investigated the physicochemical properties of lactitol for a long period and conducted earnest researches after the crystals of lactitol having excellent properties.

As a result thereof, we have discovered, upon crystallization of lactitol from an aqueous lactitol solution, the trihydrate crystal of lactitol which has been described in no literature and has excellent properties for applications, a crystalline mixture solid containing it and a process for producing them, and we have succeeded in the advantageous production of the trihydrate crystal of lactitol and the crystalline mixture solid containing it in an industrial scale. Thus, we have accomplished the present invention.

SUMMARY OF THE INVENTION

In other words, the present invention is the trihydrate crystal of lactitol which is represented by the molecular formula $C_{12}H_{24}O_{11} \cdot 3H_2O$ and has a melting point of 52–56° C. or a crystalline mixture solid containing it and a process for producing them.

The physico-chemical properties of the trihydrate crystal of lactitol according to the present invention is explained below.

(1) Elementary analysis
  Observed values: C=36.1%, H=7.6%, O=56.3%
  Calculated values: C=36.2%, H=7.6%, O=56.2%

(2) Molecular weight
  398.4

(3) Melting point
  52.0–56.4° C. (measured by visual observation by heating with a programming rate of 0.2° C./min starting from a temperature below the melting point)

(4) Differential scanning calorimetry
  Maximum endotherm=58–65° C. (measured at a programming rate of 10° C./min with a differential scanning calorimeter)

(5) Specific rotation
  $[\alpha]_D^{20} = +12.35°$ (0.1g in 1 cc of water)

(6) Ultraviolet absorption

No characteristic absorption on the measurement of an aqueous solution.

(7) Infrared absorption spectrum

A 10 mg portion of the powder of the trihydrate crystal of lactitol and 440 mg of dry KBr were mixed by agitation to make a transparent tablet (thickness, cir. 0.6 mm) for the measurement of infrared absorption spectrum. The results are shown in Table 1.

Table 1: Wave length at which the absorption of infrared rays are observed
3100–3500 (nm)
2840–2920
1600–1650
1200–1430
1000–1100

(8) Solubility

The solubility of the trihydrate crystal of lactitol in 100 g of water at 25° C. is about 160 g.

(9) Physical property, color of the material

The crystal is colorless transparent, and fine crystals are of white powder. It has a sweetness of 35–40% based on sugar and is odorless. It has no deliquescency and substantially no hygroscopicity thus exhibiting only a weight increment within the range of error upon storage at a temperature of 30° C. and a relative humidity of 72% for 24 hours.

After drying under 720–740 mmHg at 80° C. for 3 hours, a weight reduction of about 13.5% is observed.

(10) Solubilities in a variety of agents

Easily soluble in water, 0.1 N NaOH and 0.1 N HCl; soluble in methanol;
sparingly soluble in ethanol; and
insoluble in chloroform and ethyl acetate.

(11) X-ray crystallographic structure analysis

As a result of X-ray crystallographic structure analysis with use of the single crystal obtained from the trihydrate crystal of lactitol of the present invention, it was found that the crystal belongs to the rhombic system, and the unit lattice contains 4 lactitol molecules and 12 water molecules. The unit lattice had a dimension of $a = 10.152$ Å, $b = 21.3029$ Å and $c = 8.301$ Å and a unit lattice volume of 1795 Å$^3$. The crystal had a calculated density of 1.474 g/cm$^3$ and a space group of P2$_1$2$_1$2$_1$. The crystal structure is illustrated in FIG. 1.

From the above-described results, it is judged that the trihydrate crystal of lactitol of the present invention and the crystalline mixture solid containing it are a novel trihydrate crystal of lactitol and a novel crystalline mixture solid containing it which are obviously different from the materials described in literature.

Processes for producing the trihydrate crystal of lactitol of the present invention and the crystalline mixture solid containing it are described below.

A lactitol solution for crystallization used in the present invention must only crystallize the trihydrate crystal of lactitol of the present invention irrelative to the processes for producing lactitol.

The process for crystallization of the trihydrate crystal of lactitol of the present invention preferably comprises adding to a lactitol solution in a concentration of 60–85% by weight at 0° C. or more a seed crystal having 0.01–20% by weight of a solid content corresponding to the solution at a temperature of 0–30° C. and cooling under the slow agitation condition. The mascuite can be thus formed.

In this connection, an organic solvent such as ethanol or acetone can also be present in order to control the supersaturation degree of the viscosity of the solution.

Thus, the trihydrate crystal of lactitol of the present invention or the crystalline mixture solid containing it can be crystallized relatively easily by adding to a supersaturated lactitol solution a trihydrate crystal of lactitol or a crystalline mixture solid containing it as a seed crystal.

For the process for producing the trihydrate crystal of lactitol of the crystalline mixture solid containing it from the resultant mascuite suffices a process whereby the aimed product of the present invention can be collected. When the crystallized mascuite has little water cotent, it can be solidified as such. When the mascuite has a large amount of water, it is also possible to collect the trihydrate crystal of lactitol.

As the process for producing the trihydrate crystal of lactitol, it is possible to use well-known methods such as a variety of solid incorporating or solid separating methods, for example a kneading method, a block grinding method, a fluid granulation method, a spray-drying method or the like.

Specifically, the solid separating method is usually a method for separating the mascuite into a trihydrate crystal of lactitol and a solid by a centrifuge. It is also possible, if necessary, according to the solid separating method to wash easily the crystal with a small amount of water, for example, by spraying cool water, and thus such a method is suited for the production of a trihydrate crystal of lactitol having a higher purity and a melting point of 52–56° C.

Other methods such a kneading, block grinding, fluid granulation and spray-drying do not isolate the solid, and thus the crystalline mixture solid obtained may contain in addition to the trihydrate crystal of lactitol of the present invention a trace amount of the known dihydrate crystal of lactitol or other sugar alcohols such as lactulitol, mannitol, sorbitol or the like as a crystalline mixture solid component.

The kneading method as one of the solid incorporating methods, for example, comprises cooling slowly a lactitol solution having a water content of 15–40% in a kneader, adding a seed crystal having 5–50% by weight of a solid content corresponding to the solution at a temperature of or less than the melting point of the trihydrate crystal of lactitol, preferably 0–30° C. or without the addition of the seed crystal, stirring the mixture, and forming the mixture into a variety of shapes such as powder, granules, globes, rods, plates, cubes or the like to produce the powder or the molded products of the crystalline mixture solid containing the trihydrate crystal of lactitol.

The trihydrate crystal of lactitol or the crystalline mixture solid containing it according to the present invention have excellent properties as compared with the conventional anhydrous lactitol or dihydrate crystal of lactitol.

For example, when compared with the anhydrous lactitol, the trihydrate crystal is advantageous in the several points that it has a moderately low melting point, is dried by relatively easy procedures and has substantially no hygroscopicity, so that a relatively cheap packaging material can be used.

When compared with the dihydrate crystal of lactitol or the monohydrate crystal of lactitol, the trihydrate crystal of lactitol according to the present invention is advantageous in that it has an extremely low melting point of 52–56° C., so that it is dissolved smoothly on eating and thus has a good sweetness and mouth feel or it can be changed into syrup upon powdering on a warm dish at a temperature of 50°-70° C.

Thus, it can be used advantageously for the applications such as foods, cosmetics, pharmaceutical products, chemical materials and the like.

The trihydrate crystal of lactitol can be used, if necessary, in admixture with appropriate amounts of one or more of other sweeteners such as starch syrup solid, glucose, maltose, high fructose corn syrup, sucrose, honey, maple sugar, sorbitol, dihydrocharcone, stevioside, α-glycosyl stevioside, glycyrrhizin, saccharin, aspartame, glycine, alanine or the like. It can also be used in admixture with fillers such as dextrin, starch, polydextrose, lactose or the like.

Also, among the trihydrate crystal of lactitol according to present invention and the crystalline mixture solid containing it, the powder can be optionally used intact or, if necessary, mixed with fillers, vehicles, binders, disintegrating agents or the like and then formed into shapes such as granules, globes, tablets, rods, plates, cubes or the like.

Since, the trihydrate crystal of lactitol of the present invention and the crystalline mixture solid containing it, like other lactitols or lactitol crystals, are hardly digested or absorbed by the digestive system, it is possible to reduce the calorie of foods and drinks which is sweetened by the addition of the trihydrate crystal of lactitol of the present invention and the crystalline mixture solid containing it.

Thus, the invention crystal of lactitol according to present invention and the crystalline mixture solid containing it can be utilized as a low-caloric sweetener for diabetics, obese persons and those whose caloric-intake are restricted or for giving a sweet flavor to low-caloric foods such as beauty diets, health foods or dietaries.

Moreover, the trihydrate crystal of lactitol according to present invention and the crystalline mixture solid containing it have the properties that they are selectively utilized by *Lactobacillus bifidus* and are hardly fermented by cariogenic bacteria, so that they can be also used as a *Lactobacillus bifidus* growth activator or as a low-cariogenic sweetner.

Thus, the tiyhydrate crystal of lactitol according to present invention and the crystalline mixture solid containing it are suited for sweetening of low-cariogenic foods and drinks such as confectioneries, for example, chewing gum, chocolate, biscuit, cookie, caramel, and candy; and soft drinks, for example, cola drinks, cider, juice, coffee and yoghurt drinks. They are also suited for sweetening of cosmetics and drugs for preventing caries such as gargle and toothpaste.

The sweetness of the trihydrate crystal of lactitol according to present invention and the crystalline mixture solid containing it are well harmonized with a variety of materials which have other tastes such as sourness, salty taste, astringent taste, deliciousness or bitter taste, and have high resistance to acid or heat, so that they can be used optionally not only for the above-mentioned special cases but also for the sweetening or improving the tastes or the qualities of usual foods and drinks.

For instance, they can be used optionally in various seasonings such as soy sauce, soy sauce powder, soy sauce paste "MISO", soy sauce paste powder, unrefined soy "MOROMI", salted meat, a variety of fish flours, mayonnaise, dressing, vinegar, vinegar sauce tasted with sake and soy, vinegar powder, extracts for Chinese-style foods, soup for tempura, soup for noodles, sauce, catchsup, sauce for roast meat, curry roux, extract for stew, extract for soup, extract for stock, mixed seasoning, nucleic acid type seasoning, sweet sake "MIRIN", new type sweet sake, table sugar, coffee sugar, fondant or the like.

They can be also used optionally as sweeteners or agents for improving the tastes or qualities of usual foods and drinks in various Japanese-style confections such as cracker, rice-cake cubes, millet-and-rice cake, rice cakes, bun with a bean-jam filling, sweet rice jelly, bean jams, fine sweet paste, transparent sugar cube "KINGYOKU", jelly, castella, starch based candy and the like; confections such as bread, biscuit, cracker, cookie, pie, pudding, butter cream, custard cream, cream puff, waffle, sponge cake, doughnut, chocolate, chewing gum, caramel, candy and the like; syrup preserves such as fruit preserved in syrup, crystal sugar-egg white concentrate preserved in syrup "KORIMITSU" and the like; pastes such as flour paste, peanut paste, fruit paste and the like; processed foods of fruits or vegetables such as jam, marmalade, preserves, bonbon and the like; processed crop foods such as bread, noodles, rice, artificial meat and the like; pickles such as sliced vegetable pickled in soy sauce, fresh radish pickles, sliced vegetable root pickles, pickled scallions and the like; pickle additives such as an additive for pickled radish, an additive for pickled white rape and the like; meat products such as ham, sausage and the like; fish products such as fish ham, fish sausage, boiled fish paste, cylindrical boiled fish paste, tempura and the like; various seasoned marine products such as seasoned sea urchin egg, salted cuttlefish guts, sliced tangle with sour taste, sliced dry cuttlefish, dried MIRIN-seasoned swellfish and the like; dried laver, foods boiled down in soy sauce made of materials such as edible wild plants, dried cuttlefish, small fish, shell or the like; daily dishes such as cooked beans, potato salad, tangle roll and the like; bottled or canned foods such as dairy products, fish, meat, fruits or vegetables; alcoholic drinks such as synthetic wine, fruit wine, whisky and brandy, and the like; soft drinks such as coffee, cocoa, juice, carbonated drinks, lactic acid drinks and the like; premixed type powders such as pudding mix, pancake mix and the like; and convenience-type foods and drinks such as juice, coffee, adzuki-bean soup with rice cake, soup and the like.

The trihydrate crystal of lactitol according to present invention and the crystalline mixture solid containing it have sparing hygroscopicity and good fluidity, and thus they can be advantageously used also as an antiadhesion agent or a slippage improver, for example, in the case of chewing gum, sliced tangle with sour taste or the like by covering the surface of these products with the trihydrate crystal of lactitol according to present invention and the crystalline mixture solid containing it.

They can also be used for improving the tastes of pet feeds or foods for cattle, fowl, honey bee, silkworm, fish, dogs or cats, or for activating the growth of *Lactobacillus difidus* of animals.

In this connection, they can be optionally used in a variety of forms of solid, paste, liquid or the like as the taste improving agents, flavoring agents or quality improving agents of table luxuries, cosmetics or drugs such as tobacco, toothpaste, lipstick, lipcream, drug for internal administration, troche, cod-liver oil drop, oral refreshing agent, cachou, gargle and the like.

The trihydrate crystal of lactitol according to present invention and the crystalline mixture solid containing it can be formed by moistening them and compression molding under a low pressure into any desirable shapes, for example, of cube, fish, flower or the like as in the case of the molded sugar prepared from granulated sugar, so that molded sweeteners suited for coffee, tea or the like.

In this connection, they can be optionally formed with incorporating a variety of saccharides or artificial sweetners for increasing sweetness, colored with a variety of food dyes or formed with incorporating a variety of flavoring agents.

On the use of flavors, it is also possible to form a clathrate by incorporating these flavors into a clathrate compound such as cyclodextrin or the like.

The trihydrate crystal of lactitol of the present invention can be easily prepared by massive crystals like sugar, and thus it can be also used as a transparent or translucent non-hygroscopic sweetener in place of candy sugar or coffee sugar.

Moreover, the trihydrate crystal of lactitol and the crystalline mixture solid containing it can incorporate with, for example, vitamins, antibiotics or microorganisms of Lactobacillus genus and is formed into a variety of shapes such as granules or tablets to use for a variety of applications.

DESCRIPTION OF THE PREFERRED EMBODIMENTS

Figure 1:
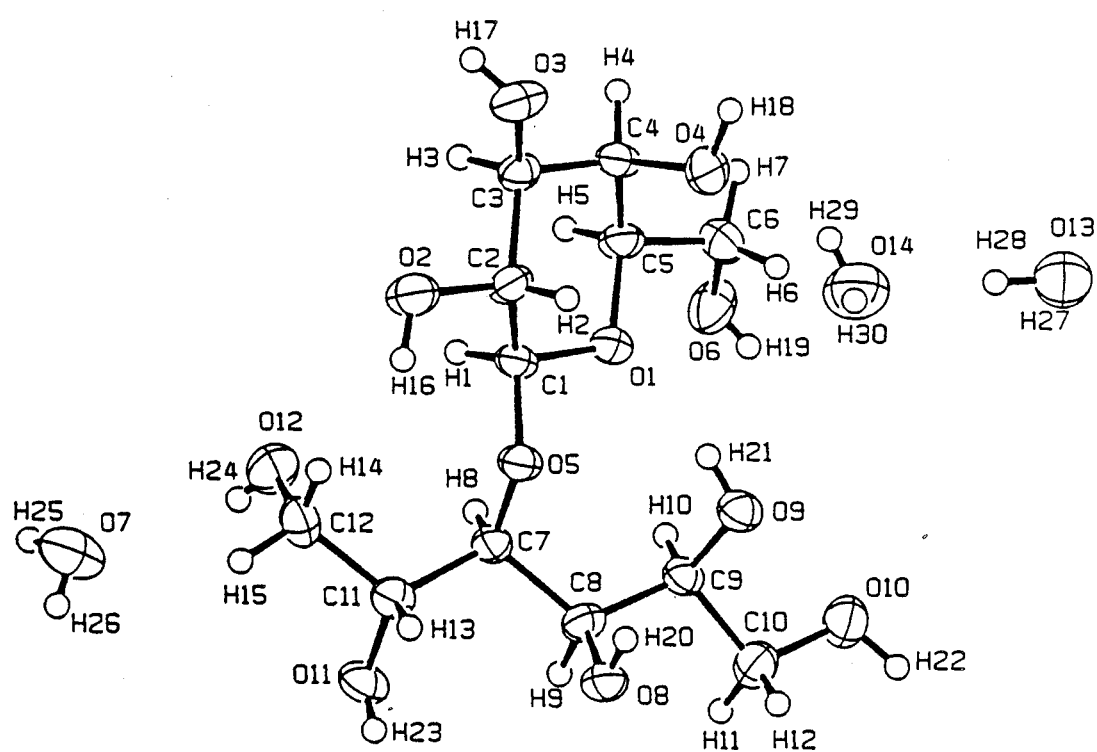
FIG. 1 is an illustration of the X-ray crystallographic structure analysis of the trihydrate crystal of lactitol of the present invention.

The present invention is further explained below with reference to examples, but it should construed that the invention is not limited to these examples.

In the following examples, all percentages means % by weight unless otherwise specified.

EXAMPLE 1

A 200 g portion of an aqueous lactitol solution having a purity of 99.9% and a concentration of 82% was placed in a stainless tray and cooled from a temperature of 50° C. to 10° C. over a period of 20 hours to give a variety of crystal blocks. Among the crystal blocks, the one in which needle crystals had been formed radially was taken out and put on each of the plates which was controlled at a predetermined constant temperature to measure the melting point by observing whether it melted or not. As a result the melting point was 54° C.

EXAMPLE 2

A 80 g portion of an aqueous lactitol solution having a purity of 99.9% and a concentration of 80% was placed in a laboplastomill, and 17 g of the crystal obtained by the method in Example 1 was added at 10° C. The mixture was kneaded at a rate of 40 rpm for 10 min to give 90 g of a crystalline mixture solid containing the trihydrate crystal of lactitol of the present invention. The melting point of the product measured by placing it on each of the plates which was controlled at a predetermined constant temperature was 52.2° C.

The product is substantially non-hygroscopic, melts at an appropriate temperature and can be easily prepared, so that it can be advantageously used as a sweetener or a quality improver of a variety of foods and drinks, cosmetics, drugs or the like, or as a raw material for chemical industry.

EXAMPLE 3

A 840 g portion of an aqueous lactitol solution having a concentration of 75.0% (lactitol purity, 99.8%) was cooled gradually starting from 80° C., 0.9 g of a seed crystal (product obtained by the method in Example 2) was added to the solution at 15° C., and the mixture was cooled under stirring for 20 hours to give a mascuite.

The mascuite was centrifugalized to give about 340 g (wet weight) of a crystal and 497 g of a filtrate having a concentration of 67.0%.

The crystal thus obtained was dried at a temperature of 20° C. for 18 hours by a cold air dehumidifying dryer to give the trihydrate crystal of lactitol of the present invention.

The melting point measured in the same manner as in Example 1 was 55.8° C.

Elementary analysis gave the values of C=36.1%, H=7.6% and O=56.3%, while the theoretical values were C=36.2%, H=7.6% and O=56.2%.

As a result of the differential scanning calorimetry (referred to hereinafter as DSC), the maximum endotherm at a programming rate of 10° C./min was 63.0° C.

EXAMPLE 4

A 72 g portion of an aqueous lactitol solution having a purity of 99.9% and a concentration of 79% was placed in a laboplastomill, and 18 g of the crystalline mixture solid obtained by the method in Example 2 was added at 5° C. The mixture was kneaded at a rate of 40 rpm for about 3 min to give a crystalline mixture solid containing the trihydrate crystal of lactitol of the present invention.

As a result of measuring the melting point of the product measured in the same manner as in Example 1, the melting point was 53.1° C. and the maximum endotherm by DSC was 59.4° C.

EXAMPLE 5

A 450 g portion of an aqueous lactitol solution having a concentration of 70.0% (lactitol purity, 99.8%) was cooled gradually starting from 60° C., and 0.5 g of the seed crystal (obtained by the method in Example 2) was added at a temperature of 10° C. The mixture was cooled under stirring for 20 hours to give a mascuite.

The mascuite was centrifugalized to give 92 g (wet weight) of a crystal and 351 g of a filtrate having a concentration of 54.2%.

The crystal thus obtained was dried at a temperature of 20° C. for 18 hours by a cold air dehumidifying dryer to give the trihydrate crystal of lactitol of the present invention.

The measurement of the melting point and the maximum endotherm by DSC gave 56.0° C. and 64.2° C., respectively.

EXAMPLE 6

A 200 g portion of an aqueous lactitol solution having a lactitol purity of 99.0% and a concentration of 83.0% was cooled gradually starting from 80° C. to 15° C. and charged into a stainless tray, 10 g of the crystalline mixture solid obtained by the method in Example 2 was added and was thoroughly dispersed. The mixture was left standing at room temperature over night to give massive crystals in the form of blocks.

The messive crystals in the form of blocks was ground to give the powder of the crystalline mixture solid containing the trihydrate crystal of lactitol of the present invention. The measurement of the melting point and maximum endotherm by DSC gave 55.0° C. and 60.0° C., respectively.

EXAMPLE 7

A 100 parts by weight portion of the crystalline mixture solid containing the trihydrate crystal of lactitol obtained by the method in Example 3 and 1 part by weight of saccharin were mixed homogeneously, and a small amount of an aqueous lactitol solution having a concentration of about 75% was sprayed to give a moisture to the mixture. The mixture was then charged in a molder for cubic sugar, pressure molded and removed from the mold to give a solid sweetener composition which was formed in a shape of cube.

The composition is a sweetener having a sweetness of about 1.8 times based on sugar and substantially no hygroscopicity and being tasty and good in shelf stability, and thus it is substantially a low caloric sweetener which has no cariogenicity.

EXAMPLE 8

Forty parts by weight of cacao paste, 10 parts by weight of cacao butter, 50 parts by weight of the trihydrate crystal of lactitol obtained by the method in Example 2, 0.5 part by weight of aspartame and 0.5 part by weight of lecithin were mixed, and the mixture was ground into fine powder in a refiner, then placed in a conche and kneaded at a temperature of 50° C. for 24 hours.

Next, the mixture was charged into a mold under cooling to 31° C. and solidified at 10° C.

The product has not hygroscopicity and thus is useful as a low cariogenic chocolate having a good quality of sweetness.

EXAMPLE 9

Fifty parts by weight of aspirin, 15 parts by weight of the powder of the crystalline mixture solid containing the trihydrate crystal of lactitol obtained by the method in Example 3 and 4 parts by weight of corn starch were thoroughly mixed, and tablets having a thickness of 5 mm and a diameter of 6 mm were produced with a tablet machine.

The tablet is non-hygroscopic and had sufficient physical strength and a good disintegrating ability in water.

EXAMPLE 10

Ninety eight parts of the crystalline mixture solid containing the trihydrate crystal of lactitol obtained by the method in Example 1 was heated to 70° C. for 5 minutes, and 1 part of malic acid, 0.25 part of cherry perfume and 0.4 part of a coloring matter were added with stirring. The mixture was then formed into a cherry candy.

The candy was a good flavoring candy in which the odor of the cherry perfume are not impaired.

What we claim is:

1. A trihydrate crystal of lactitol having a molecular formula $C_{12}H_{24}O_{11}\cdot 3H_2O$ and a melting point of 52–56° C.

2. A crystalline mixture solid consisting essentially of a trihydrate crystal of lactitol having a molecular formula $C_{12}H_{24}O_{11}\cdot 3H_2O$ and a melting point of 52–56° C.

3. A trihydrate crystal of lactitol according to claim 1, wherein said trihydrate crystal of lactitol has a purity of lactitol of 95% by weight or more based on the dry solid.

4. A crystalline mixture solid consisting essentially of a trihydrate crystal of lactitol according to claim 2, wherein said crystalline mixture solid consisting essentially of a trihydrate crystal of lactitol has a purity of lactitol of 95% by weight or more based on the dry solid.

5. A composition comprising a trihydrate crystal of lactitol according to claim 1.

6. A composition comprising a crystalline mixture solid consisting essentially of a trihydrate crystal of lactitol according to claim 2.

7. A trihydrate crystal of lactitol according to claim 1, wherein said trihydrate crystal of lactitol is molded.

8. A crystalline mixture solid consisting essentially of a trihydrate crystal of lactitol according to claim 2, wherein said crystalline mixture solid consisting essentially of a trihydrate crystal of lactitol is molded.

* * * * *